(12) United States Patent
Wix et al.

(10) Patent No.: US 9,890,098 B2
(45) Date of Patent: Feb. 13, 2018

(54) PROCESS FOR THE PRODUCTION OF SYNTHESIS GAS

(71) Applicant: Haldor Topsøe A/S, Kgs. Lyngby (DK)

(72) Inventors: Christian Wix, Nærum (DK); Ib Dybkjaer, Copenhagen (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 15/103,010

(22) PCT Filed: Dec. 11, 2014

(86) PCT No.: PCT/EP2014/077378
§ 371 (c)(1),
(2) Date: Jun. 9, 2016

(87) PCT Pub. No.: WO2015/086744
PCT Pub. Date: Jun. 18, 2015

(65) Prior Publication Data
US 2016/0304424 A1    Oct. 20, 2016

(30) Foreign Application Priority Data
Dec. 12, 2013 (DK) .................................. 2013 70765

(51) Int. Cl.
*C07C 29/151* (2006.01)
*C10G 2/00* (2006.01)
(Continued)

(52) U.S. Cl.
CPC ............ *C07C 29/1518* (2013.01); *C01B 3/38* (2013.01); *C01B 3/50* (2013.01); *C01B 3/506* (2013.01); *C07C 1/0485* (2013.01); *C10G 2/30* (2013.01); *C10L 3/08* (2013.01); *C01B 2203/0233* (2013.01); *C01B 2203/0244* (2013.01);
(Continued)

(58) Field of Classification Search
CPC .... C01B 2203/0233; C01B 2203/0244; C01B 2203/04; C01B 2203/0415; C01B 2203/0475; C01B 2203/0495; C01B 2203/061; C01B 2203/062; C01B 2203/1247; C01B 2203/127;
(Continued)

(56) References Cited

U.S. PATENT DOCUMENTS

2002/0006968 A1    1/2002  Abbott
2004/0057898 A1*   3/2004  Singh ..................... B01J 8/067
                                                                423/652
(Continued)

FOREIGN PATENT DOCUMENTS

WO    WO 2006/042986 A1    4/2006

*Primary Examiner* — Jafar Parsa
(74) *Attorney, Agent, or Firm* — Blank Rome LLP

(57) ABSTRACT

Process for the production of a synthesis gas for use in the production of chemical compounds from a hydrocarbon feed stock containing higher hydrocarbons comprising the steps of: (a) in a pre-reforming stage pre-reforming the feed stock with steam to a pre-reformed gas containing methane, hydrogen, carbon monoxide and carbon dioxide; and (b) cooling the pre-reformed gas to below its dewpoint and removing condensed water; and (c) reducing the amount of carbon dioxide the in the pre-reformed gas from step (b) to obtain a module of $(H_2-CO_2)/(CO+CO_2)$ of between 1.0 and 3.8 in the pre-reformed gas.

18 Claims, 2 Drawing Sheets

Figure 1:
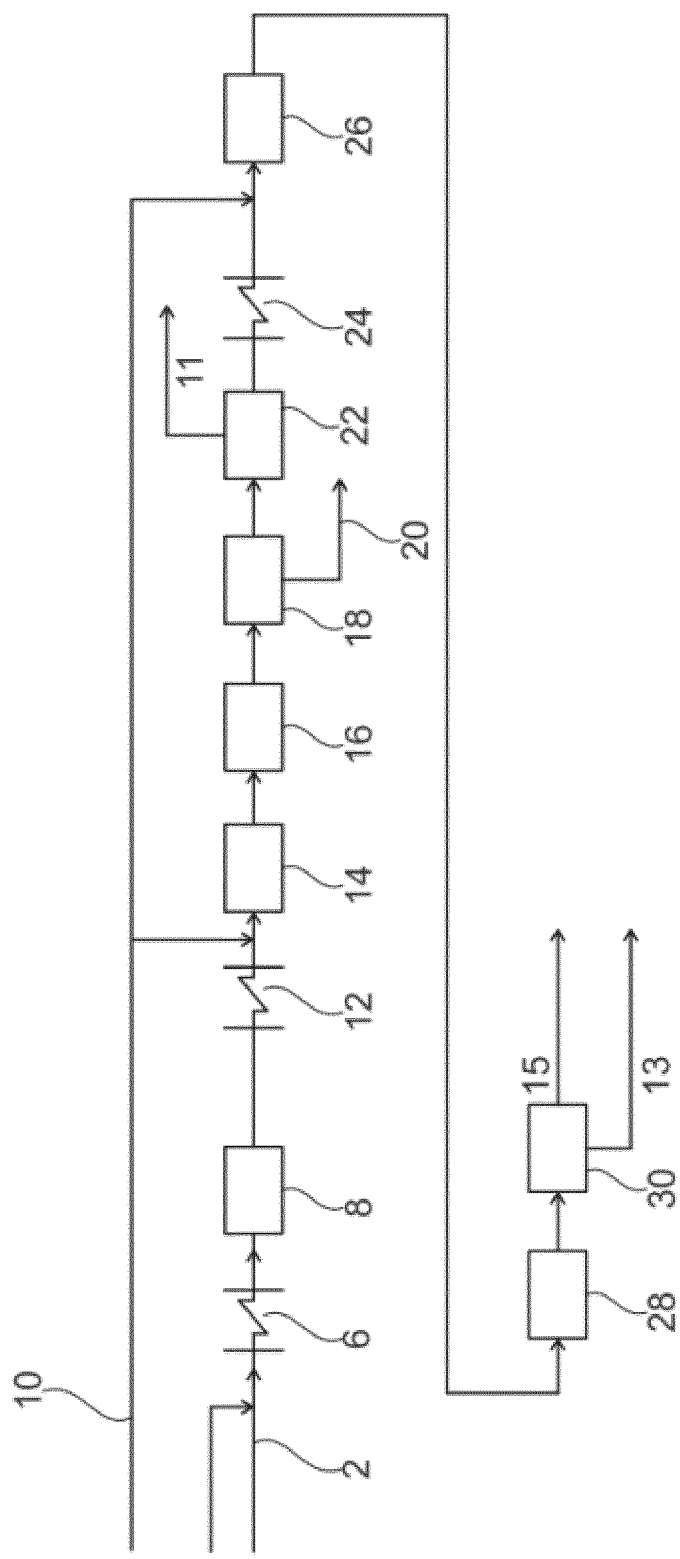

(51) Int. Cl.
*C10L 3/08* (2006.01)
*C07C 1/04* (2006.01)
*C01B 3/50* (2006.01)
*C01B 3/38* (2006.01)

(52) U.S. Cl.
CPC .. *C01B 2203/04* (2013.01); *C01B 2203/0415* (2013.01); *C01B 2203/0475* (2013.01); *C01B 2203/0495* (2013.01); *C01B 2203/061* (2013.01); *C01B 2203/062* (2013.01); *C01B 2203/127* (2013.01); *C01B 2203/1247* (2013.01); *C01B 2203/142* (2013.01); *C01B 2203/143* (2013.01); *C01B 2203/146* (2013.01); *C01B 2203/148* (2013.01); *C10L 2290/06* (2013.01)

(58) Field of Classification Search
CPC ........ C01B 2203/142; C01B 2203/143; C01B 2203/146; C01B 2203/148; C10G 2/30
See application file for complete search history.

(56) References Cited

U.S. PATENT DOCUMENTS

2005/0220703 A1 10/2005 Ihara et al.
2006/0135629 A1 6/2006 Abbott et al.

\* cited by examiner

PROCESS FOR THE PRODUCTION OF SYNTHESIS GAS

The present invention relates to a process for the production of a synthesis gas for use in the preparation of synthetic natural gas, hydrocarbons and oxygenated hydrocarbons by known processes to prepare these compounds from synthesis gas.

The invention concerns in particular the conversion of a hydrocarbon feed stock with a high content of higher hydrocarbons, like associated gas, shale gas or natural gas liquids to synthesis gas.

Associated gas, also known as flare gas, is a form of natural gas with a high content of higher hydrocarbons, which is commonly found associated with deposits of petroleum.

In the past most of the associated gas was flared as it was costing more to treat it and transport it to market places than its potential trading value.

Flaring million tons per day of associated gas has and is still contributing to a major source of carbon dioxide emission.

In particular, associated petroleum gas (APG) is a gas dissolved in oil also known to have a high content of higher hydrocarbons. The disposal of APG had typically been solved by flaring.

Shale gas is known to have a high content of higher hydrocarbons, which makes it problematic to use this gas in chemical processes.

Use of gases with a high concentration of higher hydrocarbons for the production of synthesis gas is problematic because they require a high steam to carbon ratio (S/C) in the steam reforming section of the steam reforming process to avoid carbon formation on the reforming catalyst. High S/C ratios imply a need for larger steam reforming reactors.

To keep the S/C ratio within acceptable ranges, use of heavy gases for the preparation of synthesis gas requires usually removal of most of the higher hydrocarbons by cryogenic processes or membrane separation processes. These processes form a secondary product consisting of a mixture of higher hydrocarbons, which in many cases is problematic.

Another problem may arise when the amount of gas containing higher hydrocarbons is simply too small to make it feasible to build a pipeline and the transportation becomes too expensive by other means. The gas is therefore flared. In some cases where a natural gas pipeline is present, the pipeline specification does not allow significant amounts of higher hydrocarbons in the gas. In this case the conversion of higher hydrocarbons to synthetic natural gas or to compounds that can be transported in the oil pipeline solves the problem.

U.S. Pat. No. 7,879,919 discloses a process for producing hydrocarbons from natural gas, including separation of olefins, LPG, naphtha and inerts in a cryogenic unit to form methane. The methane product is employed in the preparation of synthesis gas for downstream FT synthesis.

Conventional processes comprise production of synthesis gas by steam reforming (SMR), 2-step reforming (SMR+ oxidative catalytic reforming), or catalytic partial oxidation (ATR, CPO, PDX), optionally in combination with heat exchange reforming. Each of these reforming technologies defines critical steam content in the feed, required to avoid carbon formation or other undesirable phenomena in the reforming process. Optimum performance is obtained by operating marginally above the critical steam content.

Methanol synthesis requires a synthesis gas with a module $M=(H_2-CO_2)/(CO+CO_2)$ of about 2. When 2-step reforming is used, the module is adjusted by adjusting the size of the SMR. When higher hydrocarbons or a high concentration of $CO_2$ is present in the feed, the required size of the SMR increases. This is undesirable, especially at high capacity due to the high cost of the large capacity SMR. It is desirable to have a high $CO/CO_2$-ratio in the synthesis gas to methanol synthesis, since this increases reaction rate and equilibrium conversion and reduces catalyst deactivation rate.

FT-synthesis (Fischer-Tropsch) requires a synthesis gas with a $H_2/CO$-ratio of about 2. The ratio can be adjusted to the desired value by removing $H_2$ from the raw synthesis gas or by recycling tail gas from the FT-synthesis to the reforming step.

When a feed gas contains high concentration of higher hydrocarbons and/or $CO_2$, ATR (autothermal reforming) will produce a synthesis gas with lower $H_2/CO$ ratio and higher $CO_2$-content than with lean natural gas as feed. $CO_2$ is inert in the FT-synthesis process and therefore undesired. Low $H_2/CO$— ratio means that less tail gas is required for ratio-adjustment. Therefore, more tail gas must be discarded. This reduces the overall efficiency of the production process and is therefore undesirable.

US patent application 2006/0194889 mentions $CO_2$ removal from syngas to produce syngas with various $(H_2-CO_2)/(CO+CO_2)$ modules depending on downstream application such as FT, MeOH etc. The $CO_2$ removal is in this process conducted on produced syngas.

Similarly, US 2006/0135629, US 2002/0006968, US 2005/02220703 disclose processes in which water and $CO_2$ removal is conducted on produced syngas, i.e. on gas resulting from pre-reforming (as optional stage) followed by reforming in a tubular reformer or heat exchange reformer and subsequent secondary reforming or autothermal reforming.

WO 2006/042986 discloses also a process in which synthesis gas from a steam methane reformer (not a pre-reformer) is subjected to water removal and then $CO_2$ removal. The $CO_2$ is recycled to the steam methane reformer.

EP 2261308 describes a process for methanation where a syngas from a gasifier is passed through a shift conversion step, then through $CO_2$ removal and finally methanation to produce SNG. The syngas produced for methanation has $M=(H_2-CO_2)/(CO+CO_2)$ greater than 3.0 and is combined in the methanation stage with a gas having a $M=(H_2-CO_2)/(CO+CO_2)$ lower than 3.0.

It would desirable to utilize feed stocks with a high content of higher hydrocarbons for the production of useful chemical compounds without the above problems.

It is thus the general object of the invention to provide a process for utilization of feed stocks like the above mentioned gases with a high content of heavy hydrocarbons for the preparation of a synthesis gas, which is in particular useful for the production of synthetic natural gas (SNG) by the known methanation process, liquid hydrocarbons by the Fischer-Tropsch (FT) synthesis or by the gasoline process, and methanol by known processes.

This and other objects are solved by the present invention as defined by the following features in correspondence with the appended claims.

FEATURES OF THE INVENTION

1. Process for the production of a synthesis gas for use in the production of chemical compounds from a hydrocarbon feed stock containing higher hydrocarbons comprising the steps of:

(a) in a pre-reforming stage pre-reforming the feed stock with steam to a pre-reformed gas containing methane, hydrogen, carbon monoxide and carbon dioxide; and (b) cooling the pre-reformed gas to below its dew point and removing condensed water; and (c) reducing the amount of carbon dioxide in the pre-reformed gas from step (b) to obtain a module of $(H_2-CO_2)/(CO+CO_2)$ of between 1.0 and 3.8 in the pre-reformed gas.

2. Process according to feature 1 comprising the further step of a hydrodesulfurization stage removing sulfur compounds in the hydrocarbon feed stock prior to the pre-reforming stage in step (a).

3. Process according to feature 1 or 2, wherein the pre-reforming stage comprises pre-reforming in at least a first and second pre-reformer stage connected in series.

4. Process of feature 3, wherein a part of the feed stock is by-passed the at least first pre-reformer stage and mixed with pre-reformed gas withdrawn from the first pre-reformer stage prior to being further pre-reformed in the second pre-reformer stage.

5. Process of feature 3, wherein the steam is solely added to the feed stock passed to the at least first pre-reformer stage.

6. Process according to anyone of features 1 to 3, wherein a part of the pre-reformed gas is recycled to the inlet of the first pre-reforming stage.

7. Process according to feature 6, wherein the part of the pre-reformed gas is recycled to the inlet of the first pre-reforming stage by means of an ejector using the steam, synthetic natural gas or intermediate products as motive fluid.

8. Process according anyone of features 2 to 7, wherein a part of the pre-reformed gas is recycled to the hydrodesulfurization stage by means of an ejector using the synthetic natural gas or intermediate products as motive fluid.

9. Process according to anyone of features 1 to 8, wherein the pre-reformed gas from step (c), optionally mixed with additional steam to obtain a desired steam to carbon ratio, is further steam reformed in a steam reforming stage comprising a tubular steam reformer or an autothermal reformer or a primary steam reformer and a subsequent secondary steam reformer to obtain a steam reformed product gas.

10. Process of feature 9, wherein the steam reformed product gas is subjected to synthesis of oxygenated hydrocarbons or of liquid hydrocarbons, including the Fischer-Tropsch synthesis and synthesis of gasoline.

11. Process of feature 10, wherein tail or off-gas from the synthesis of the liquid hydrocarbons is recycled to the steam reforming stage.

12. Process of feature 9, wherein the steam reformed product gas is subjected to synthesis of oxygenated hydrocarbons.

13. Process of anyone of features 1 to 8, wherein the pre-reformed gas from step (c) is subjected to a methanation stage for the production of synthetic natural gas.

14. Process of features 8 or 13, wherein a part of the hydrogen in the pre-reformed gas is recycled to the hydrodesulfurization stage by means of an ejector using steam or synthetic natural gas as motive fluid.

15. Process according to anyone of features 1 to 14, wherein the hydrocarbon feed stock containing higher hydrocarbons is selected from associated gas or shale gas or associated petroleum gas.

16. Process according to anyone of features 1 to 14, wherein the hydrocarbon feed stock is a stream of higher hydrocarbons in the range ethane to naphtha obtained by separation from associated gas or shale gas or from any other gas containing higher hydrocarbons.

17. Process according to anyone of features 1 to 16, wherein the average number of C atoms in the hydrocarbons of the feed stock is higher than 1.5.

18. Process according to anyone of features 1 to 17, wherein the module of $(H_2-CO_2)/(CO+CO_2)$ is between 1.7 and 3.2 in the pre-reformed gas.

19. Process according to anyone of features 1 to 18, wherein the average number of C atoms in the hydrocarbons of the feed stock is higher than 2.0.

In a particular embodiment, the invention encompasses also a process according to anyone of features 1 to 16, wherein the amount of carbon dioxide the in the pre-reformed gas is reduced by means of a chemical wash or physical carbon dioxide separation.

The term "pre-reforming" and "pre-reformer" as used herein before and in the following shall mean a steam reforming process and steam reformer by which higher hydrocarbons are converted to a mixture of methane, carbon oxides and hydrogen.

As is well known for a person skilled in the art, the term "pre-reforming" shall not be exchanged with steam reforming or other reforming processes, such as steam methane reforming (SMR), autothermal and/or secondary reforming. Pre-reforming is normally conducted at temperatures in the range 375-650° C., preferably adiabatically in a fixed bed of catalyst, and its main purpose is to remove hydrocarbons higher than methane, whereas steam reforming is a subsequent stage conducted at much higher temperatures (700-1000° C.) and with the main purpose of producing a mixture of CO, $CO_2$ and $H_2$ (synthesis gas) suitable for downstream applications such as Fischer-Tropsch synthesis. Hence, the pre-reforming according to any of the above or below embodiments is preferably conducted adiabatically.

"Higher hydrocarbons" contained in the hydrocarbon feed stock employed in the process according to the invention are hydrocarbons heavier than methane.

We have found that by removing part of the amounts of carbon dioxide from the pre-reformed gas instead of from the feed gas or from the synthesis gas after a steam reforming results in less steam consumption and lower S/C ratios required in the steam reforming stage subsequent the pre-reforming stage. The volumetric flow of the effluent gas from the steam reforming stage is reduced thereby reducing the size of downstream equipment.

The provisions of features 3 to 5, which require that the feed stock is passed through at least two pre-reformers in series provides the possibility to by-pass an amount of the feed gas the first pre-reformer and mixing the pre-reformed gas with the by-passed feed gas. The gas mixture is subsequently further pre-reformed in the second pre-reformer.

As an example, in such a two-step pre-reforming lay-out the feed gas is split 60/40 vol %, where 60 vol % are introduced into the first pre-reformer and 40 vol % are by-passed. The 60 vol % feed gas to the first pre-reformer are mixed with all steam required in the complete pre-reforming stage to S/C=1.4 (molar ratio). In the second pre-reforming reactor, the by-passed 40 vol % feed stock are mixed with the pre-reformed gas from the first pre-reformer. The overall S/C is thereby reduced resulting in less steam consumption and also less $CO_2$ formation.

A part of the pre-reformed gas maybe recycled to the first pre-reformer in the pre-reforming stage.

A part of the pre-reformed gas may be further recycled to a hydrodesulfurization stage.

According to feature 7 and 8, recycling of a part of the pre-reformed gas is performed by an ejector being driven by steam as motive fluid.

Pre-reforming by using an ejector to add steam to the feed stock and thereby driving a recycle around the ejector has the benefit of lowering the temperature resulting in an increased amount of methane in the pre-reformed gas and saving of steam for a fixed S/C ratio.

Another benefit of the lowered temperature is that the required amount of water to avoid carbon formation is reduced with temperature.

Another advantage of (hot) recycle is that unconverted water in the pre-reformed gas is reused leading to an overall lower energy consumption.

One of the important steps of the inventive process is removal of water and reduction of the content of carbon dioxide being withdrawn from the pre-reforming stage. Thereby, it is advantageous to adjust the amount of removed $CO_2$ to obtain a module of $(H_2-CO_2)/(CO+CO_2)$ of between 1.0 and 3.8 in the pre-reformed gas, as required for instance in a subsequent methanation stage requiring a module of 3.0.

In a particular embodiment a portion of the pre-reformed gas bypasses the step of $CO_2$-removal and is combined with the pre-reformed gas which has been subjected to $CO_2$-removal prior to entering the methanation stage.

The pre-reformed gas may further be steam reformed in a steam reforming stage. This will be necessary for the production of oxygenated hydrocarbons, e.g. methanol and liquid hydrocarbons, including the Fischer-Tropsch synthesis and synthesis of gasoline, as mentioned in features 9 to 10. The synthesis of methanol and liquid hydrocarbons requires a module of $(H_2-CO_2)/(CO+CO_2)$ of about 2 after the final steam reforming stage.

In such applications the amount of carbon dioxide from the pre-reforming stage may adjusted to obtain a module of $(H_2-CO_2)/(CO+CO_2)$ of 3.0 corresponding to pre-reforming of pure methane and the pre-reformed gas from the carbon dioxide removal stage constitutes an attractive feed to a downstream autothermal reformer.

The above features of the process according to the invention are described in more detail in the following description by reference to the drawing, in which:

FIG. 1 shows a simplified flow scheme of a specific embodiment of the invention for the production of a synthesis gas with $CO_2$ removal from pre-reformed gas.

Figure 2:
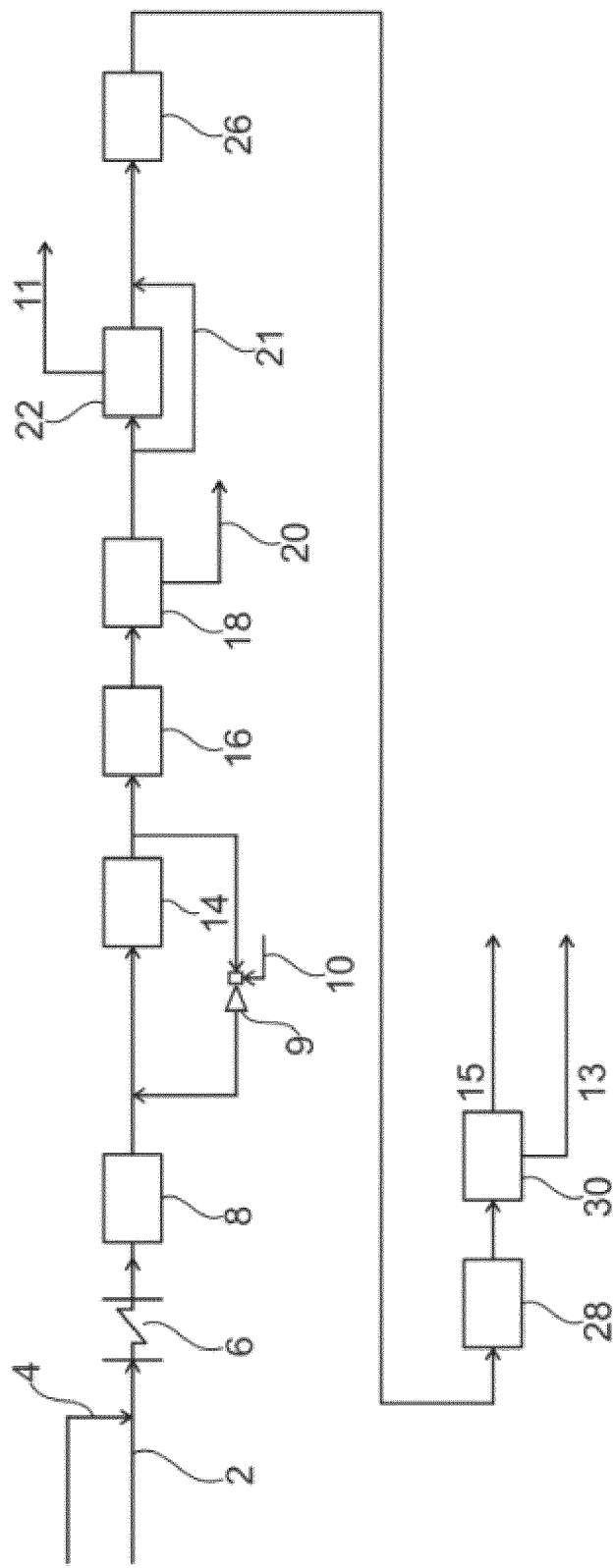

FIG. 2 shows a simplified flow scheme of a specific embodiment of the invention for the production of methane with $CO_2$ removal from pre-reformed gas Referring now to FIG. 1, natural gas feed gas 2 containing higher hydrocarbons is mixed with hydrogen from line 4 and the feed mixture is heated in heat exchanger 6 and subsequently introduced into to a hydrodesulfurization unit (HDS) 8. In HDS 8 sulfur compounds contained in the feed stock are removed by means of hydrodesulfurization by contact with a hydrogenation catalyst and a sulfur absorbent known in the art. The thus purified feed gas is heated in heat exchanger 12 and admixed with steam from line 10. The heated feed gas/steam mixture is subsequently introduced into the pre-reforming unit 14. In unit 14 the higher hydrocarbons contained in the feed gas are converted to mainly methane, as well as carbon oxides and hydrogen by contact with a pre-reforming catalyst known in the art. The pre-reformed gas withdrawn from unit 14 is subsequently cooled in cooler 16 to below the dew point of the gas and passed to separator 18. In separator 18 process condensate is separated from the pre-formed gas and passed away through line 20. The separated pre-reformed gas is then introduced into $CO_2$-removal unit 22. $CO_2$ is withdrawn via line 11. The $CO_2$ content in the pre-reformed gas is in the $CO_2$-removal unit reduced to lower than about 8 dry vol %, e.g. lower than 4 or lower than 1 dry vol % to obtain a module of $(H_2-CO_2)/(CO+CO_2)$ of between 1.0 and 3.8 depending the final use of the synthesis gas prepared by the process. The $CO_2$ removal in unit 22 is performed by means of chemical wash as in the known MDEA or Benfield process or physical solvent processes as the known Selexol® process. The $CO_2$ depleted pre-reformed gas is withdrawn from unit 22 and heated in heat exchanger 24 prior to be introduced in autothermal reformer 26 together with steam from line 10. As further an advantage of the process according to the invention the amount of steam to be added to the $CO_2$-depleted pre-reformed gas is comparatively lower than the amounts required in a process without $CO_2$ removal from the pre-reformed gas, e.g. about 0.8 or lower with $CO_2$ removal compared to the known processes without $CO_2$-removal requiring an S/C of about 1.5 (molar ratio) when using the same feed stock composition. The autothermal reformed gas withdrawn from autothermal reformer 26 is cooled below its dew point in cooler 28 and process condensate 13 is separated from the gas in separator 30 from the final synthesis gas 15.

Referring now to FIG. 2, a gas feed gas 2 containing higher hydrocarbons, mostly in the form of ethane (ethane rich gas such as associated petroleum gas, APG), is mixed with hydrogen from line 4 and the feed mixture is heated in heat exchanger 6 and subsequently introduced into to a hydrodesulfurization unit (HDS) 8. In HDS 8 sulfur compounds contained in the feed stock are removed by means of hydrodesulfurization by contact with a hydrogenation catalyst and a sulfur absorbent known in the art. The thus purified feed gas is admixed with part of the pre-reformed gas which is recycled via ejector 9 using steam 10 as motive fluid. The resulting mixture is subsequently introduced into the pre-reforming unit 14. In pre-reforming unit 14 the higher hydrocarbons contained in the feed gas are converted to mainly methane, as well as carbon oxides and hydrogen by contact with a pre-reforming catalyst known in the art. Part of the pre-reformed gas withdrawn from unit 14 is recycled via ejector 9 and the rest is subsequently cooled in cooler 16 to below the dew point of the gas and passed to separator 18. In separator 18 process condensate is separated from the pre-formed gas and withdrawn through line 20. The separated pre-reformed gas is then introduced into $CO_2$-removal unit 22. $CO_2$ is withdrawn via line 11. A portion 21 of the pre-reformed gas by-passes the $CO_2$-removal unit 22. The $CO_2$ content in the pre-reformed gas is in the $CO_2$-removal unit reduced to obtain a module of $(H_2-CO_2)/(CO+CO_2)$ of about 3.0 which is required for subsequent methanation. The $CO_2$ removal in unit 22 is performed by means of chemical wash as in the known MDEA or Benfield process or physical solvent processes as the known Selexol® process. The $CO_2$ depleted pre-reformed gas is withdrawn from unit 22 and combined with by-pass stream 21 prior to be introduced in methanator 26. The gas withdrawn from methanator 26, now having over 99 vol % methane is cooled below its dew point in cooler 28 and process condensate 13 is separated from the gas in separator 30 from the final product in the form of methane stream 15.

The invention claimed is:
1. A process for the production of a synthesis gas for use in the production of chemical compounds from a hydrocarbon feed stock containing higher hydrocarbons comprising the steps of:

(a) in a pre-reforming stage pre-reforming the feed stock with steam to a pre-reformed gas containing methane, hydrogen, carbon monoxide and carbon dioxide; and
(b) cooling the pre-reformed gas to below its dew point and removing condensed water;
(c) reducing the amount of carbon dioxide in the pre-reformed gas from step (b) to obtain a module of $(H_2-CO_2)/(CO+CO_2)$ of between 1.0 and 3.8 in the pre-reformed gas; and
(d) feeding the pre-reformed gas from step (c) to a steam reforming stage comprising a tubular steam reformer or an autothermal reformer or a primary steam reformer and a subsequent secondary steam reformer to obtain a steam reformed product gas.

2. The process according to claim 1 comprising the further step of a hydrodesulfurization stage removing sulphur compounds in the hydrocarbon feed stock prior to the pre-reforming stage in step (a).

3. The process according to claim 1, wherein the pre-reforming stage comprises pre-reforming in at least a first and second pre-reformer connected in series.

4. The process of claim 3, wherein a part of the feed stock is by-passed the at least first pre-reformer stage and mixed with pre-reformed gas withdrawn from the first pre-reformer stage prior to being further pre-reformed in the second pre-reformer stage.

5. The process of claim 3, wherein the steam is solely added to the feed stock passed to the at least first pre-reformer stage.

6. The process according to claim 1, wherein a part of the pre-reformed gas is recycled to the inlet of the pre-reforming stage.

7. The process according to claim 6, wherein the part of the pre-reformed gas is recycled to the inlet of the pre-reforming stage by means of an ejector using the steam, synthetic natural gas or intermediate products as motive fluid.

8. The process according to claim 2, wherein a part of the pre-reformed gas is recycled to the hydrodesulfurization stage by means of an ejector using the synthetic natural gas or intermediate products as motive fluid.

9. The process of claim 1, wherein the steam reformed product gas is subjected to synthesis of liquid hydrocarbons, including the Fischer-Tropsch synthesis and synthesis of gasoline.

10. The process of claim 9, wherein tail or off-gas from the synthesis of the liquid hydrocarbons is recycled to the steam reforming stage.

11. The process of claim 1, wherein the steam reformed product gas is subjected to synthesis of oxygenated hydrocarbons.

12. The process of claim 1, wherein the pre-reformed gas from step (c) is subjected to a methanation stage for the production of synthetic natural gas.

13. The process of claim 8, wherein a part of the hydrogen in the pre-reformed gas is recycled to the hydrodesulfurization stage by means of an ejector using steam or synthetic natural gas as motive fluid.

14. The process according to claim 1, wherein the hydrocarbon feed stock containing higher hydrocarbons is selected from associated gas or shale gas or associated petroleum gas.

15. The process according to claim 1, wherein the hydrocarbon feed stock is a stream of higher hydrocarbons in the range ethane to naphtha obtained by separation from associated gas or shale gas or from any other gas containing higher hydrocarbons.

16. The process according to claim 1, wherein the average number of C atoms in the hydrocarbons of the feed stock is higher than 1.5.

17. The process according to claim 1, wherein the module of $(H_2-CO_2)/(CO+CO_2)$ is between 1.7 and 3.2 in the pre-reformed gas.

18. The process according to claim 1, wherein the average number of C atoms in the hydrocarbons of the feed stock is higher than 2.0.

* * * * *